(12) United States Patent
Imanishi et al.

(10) Patent No.: US 7,074,612 B2
(45) Date of Patent: Jul. 11, 2006

(54) INSECT CELL PRIMARY CULTURE MEDIUM, EXTRACELLULAR MATRIX, AND PROCESS OF PREPARING AN INSECT CULTURE CELL LINE IN A SHORT PERIOD OF TIME USING THE MEDIUM AND MATRIX

(75) Inventors: Shigeo Imanishi, Tsuchiura (JP); Atsunobu Haga, Ryugasaki (JP); Jun Mitsuhashi, Tokyo (JP)

(73) Assignee: National Institute of Agrobiological Sciences, Tsukuba (JP)

( * ) Notice: Subject to any disclaimer, the term of this patent is extended or adjusted under 35 U.S.C. 154(b) by 63 days.

(21) Appl. No.: 10/715,361

(22) Filed: Nov. 19, 2003

(65) Prior Publication Data

US 2004/0101961 A1  May 27, 2004

Related U.S. Application Data

(62) Division of application No. 10/091,318, filed on Mar. 6, 2002, now Pat. No. 6,943,023.

(51) Int. Cl.
*C12N 5/00* (2006.01)

(52) U.S. Cl. .................. 435/325; 435/348; 435/402; 536/20

(58) Field of Classification Search ................. 435/325, 435/348, 402; 536/20
See application file for complete search history.

(56) References Cited

U.S. PATENT DOCUMENTS 6,156,330 A * 12/2000 Tsukada et al. ............. 424/408

FOREIGN PATENT DOCUMENTS

| JP | 404138169 A | * | 5/1992 |
| JP | 404293481 A | * | 10/1992 |
| JP | 405000954 A | * | 1/1993 |
| JP | 406166635 A | * | 6/1994 |

* cited by examiner

*Primary Examiner*—Leon B. Lankford, Jr.
(74) *Attorney, Agent, or Firm*—Oblon, Spivak, McClelland, Maier & Neustadt, P.C.

(57) ABSTRACT

A novel cell culture medium suitable for primary culture of insect cells, an insect-derived water-soluble chitin, and a process of preparing an insect culture cell line in a short period of time by using the insect primary culture medium and the insect-derived water-soluble chitin. The insect cell primary culture medium comprises lactalbumin hydrolysate, yeastolate, and tryptose phosphate broth as protein extracts, and polyvinylpyrrolidone as a viscosity-supplementing agent. The insect-derived water-soluble chitin is subjected to deacetylation as the sole chemical modification.

6 Claims, No Drawings

INSECT CELL PRIMARY CULTURE MEDIUM, EXTRACELLULAR MATRIX, AND PROCESS OF PREPARING AN INSECT CULTURE CELL LINE IN A SHORT PERIOD OF TIME USING THE MEDIUM AND MATRIX

BACKGROUND OF THE INVENTION

1. Field of the Invention

The present invention relates to a technique for preparing an insect culture cell system.

2. Prior Art

There are two stages in the preparation of an animal culture cell line including that of insects. The initial stage is called primary culture, and the next stage is called subculture. When a culture cell line is prepared, a target tissue is extracted from an insect of interest in an aseptic manner. The tissue is then put into a culturing flask together with a cell culture medium, and cultured for about one year, until cells emerge from the tissue section onto the flask surface and divide into sufficient numbers. The sufficiently multiplied cells are transplanted into a new flask where they are subjected to subculture, i.e., culturing of a prepared cell line.

In the prior art, a variety of insect cell media are available. Examples include Grace's media, IPL-41 media, Schneider's Drosophila media, Sf900II, TC-100 media, Sf-9 cell media, Sf-21 cell media, Express Five media, and EX-400 media. Mitsuhashi, J. et al. have prepared a medium along the line of MGM, for example, by referring to the results of insect body fluid analysis (MGM-443; Mitsuhashi, J. (1980) In: Kurstak, E., Maramorosch, K. and Dubendorfer, A. (eds) Invertebrate Systems In Vitro Elsevier/North Holland Biomedical, Amsterdam, pp. 47–58, MGM-448; Mitsuhashi, J. (1984) Zool. Sci. 1, pp. 415–419, MGM-450; Mitsuhashi, J. and Inoue, H (1988) Appl. Entomol. Zool. 23, pp. 488–490, MGM-464; Mitsuhashi, J. (2001) In Vitro Cell. Dev. Biol. 37A, pp. 330–337. MGM-443, MGM-448, MGM-450, and MGM-464 are media names.).

The present inventors have prepared MM-8 SF medium, for example (Shigeo Imanishi, "Konchu Kino Jikken-kei Oyobi Konchu Saibo Baiyo-kei No Kaihatsu: Kenkyu Seika 295" ("Development of Insect Function -Experiment System and Insect Cell Culture System: Study Results 295"), ed. by Agriculture, Forestry, and Fisheries Research Council, pp. 74–84 (1994)). These media, however, are not suitable for primary culture, and are used mostly for the subcultivation of a prepared culture cell line, i.e., for the maintenance of the cells after development of the cell line. When these media were used for primary culture, cell growth was not satisfactory, and primary culture took as long as about one year, as mentioned above. Thus, there has been no medium suitable for primary culture which enables the cells to be transferred into subculture at an early stage. Moreover, many of these media were limited for use with certain insect species. For example, the Schneider's Drosophila medium was for the culturing of cells of insects of the order Diptera, particularly fruit flies, while Sf900II, Sf-9 cell medium and Sf-21 cell medium were for the cells of insects of the order Lepidoptera, particularly inch worms. Thus, there has so far been no medium suitable for the growth of cells of insects of a wide variety of orders.

On the other hand, flasks generally used for cell culture are made of plastic, and are believed to have a coating of extracellular matrix on the plastic surface, such as, e.g., collagen I, II, III, IV, or V, fibronectin, gelatin, laminin, poly-L-lysine, Matrigel, and EHS-matrix. There are not many detailed reports about their compositions, but as to chitin and chitosan, there have been reports about an extracellular matrix extracted from crustaceans such as lobsters and crabs. These chitin and chitosan have been variously chemically modified. The extracellular matrix provides the effect of attaching a tissue to the cell culture vessel, and adhering those cells that have transmigrated from the tissue to the vessel surface for division and multiplication. However, there is a need for an extracellular matrix with a higher cell adhesion ability for good cell culture.

SUMMARY OF THE INVENTION

It is therefore an object of the present invention to provide a novel cell culture medium suitable for primary culture of insect cells. Another object of the present invention is to provide an insect-derived, water-soluble chitin that has been subjected to deacetylation as the only chemical modification. Yet another object of the present invention is to provide a process of preparing an insect culture cell line in a short period of time which utilizes the above insect cell primary culture medium and insect-derived, water-soluble chitin.

As described above, there is a need for a medium suitable for primary culture of insect cells, i.e., an insect cell medium which facilitates the division and multiplication of only those cells (primary cells) that emerged on the bottom surface of the culture flask from the sliced tissue segment after start of cell culture, thereby enabling the cells to be transferred to subculture at an early stage.

After careful examination and analysis of media suitable for primary culture which facilitate the division and multiplication of cells obtained from a tissue fragment and which enable the cells to be transferred to subculture at an early stage, the inventors arrived at the present invention after realizing that a novel medium containing certain protein extracts and a viscosity-supplementing agent was suitable for primary culture.

The inventors also carefully examined and analyzed a novel extracellular matrix to be coated on a culture vessel which is suitable for culturing insect cells. As a result, the inventors arrived at the present invention after finding that when cells are cultured in a cell culture vessel coated with an extracellular matrix comprising an insect-derived, water-soluble chitin that has not been subjected to chemical modification other than deacetylation, the attachment of the tissue onto the culture vessel can be improved and that cells that have transmigrated from the tissue also adhere to the vessel surface and divide and multiply. Furthermore, the inventors arrived at the present invention after finding that primary culture can be performed more efficiently by using a cell culture vessel which is coated with an extracellular matrix comprising an insect-derived, water-soluble chitin that has been subjected to no chemical modification, and a medium suitable for primary culture.

Namely, the present invention provides the following:

(1) an insect cell primary culture medium comprising lactalbumin hydrolysate, yeastolate, and tryptose phosphate broth as protein extracts, and polyvinylpyrrolidone as a viscosity-supplementing agent;

(2) an insect cell primary culture medium (1) comprising 1000–3000 mg/L of lactalbumin hydrolysate, 1000–3000 mg/L of yeastolate, 1000–3000 mg/L of tryptose phosphate broth, and 200–500 mg/L of polyvinylpyrrolidone;

(3) an insect cell primary culture medium (1) or (2), wherein the polyvinylpyrrolidone is polyvinylpyrrolidone K-90;

(4) an insect-derived, water-soluble chitin that has been subjected to deacetylation as the sole chemical modification;

(5) an insect-derived, water-soluble chitin (4), wherein the chitin has been derived from silkworm;

(6) an insect-derived, water-soluble chitin (5), wherein the chitin has been derived from silkworm pupa exuvia;

(7) an extracellular matrix comprising any one of the insect-derived, water-soluble chitin (4) to (6);

(8) an extracellular matrix solution for coating a culture vessel, comprising 0.001% to 1% of any one of the insect-derived, water-soluble chitin (4) to (6);

(9) an insect cell culture vessel coated with any one of the insect-derived, water-soluble chitin (4) to (6);

(10) a process of manufacturing the insect-derived, water-soluble chitin (6), which comprises extracting chitin from a silkworm pupa exuvia and deacetylating the chitin;

(11) a process of preparing an insect culture cell line in a short period of time, which uses any one of the insect primary culture cells (1) to (3), and any one of the insect-derived water-soluble chitin (4) to (6); and

(12) a process of preparing an insect culture cell line in a short period of time according to (11), wherein a vessel coated with any one of the insect-derived water-soluble chitin (4) to (6) is used, and an insect cell is cultured on any one of the insect primary culture media (1) to (3).

DESCRIPTION OF THE INVENTION

The present invention will be hereinafter described in detail.

1. Composition of the Insect Cell Primary Culture Medium According to the Invention The insect cell primary culture medium according to the present invention comprises at least a protein extract and a viscosity-supplementing agent. The primary culture medium according to the present invention may further comprise a mixed composition of inorganic salts, a sugar composition, a mixed composition of amino acids, and a mixed composition of vitamins.

Examples of the protein extract include at least lactalbumin hydrolysate, yeastolate, and tryptose phosphate broth, and may further include fetuin, cytochrome c, inosine, bovine plasma albumin V, etc. Lactalbumin, yeastolate, and tryptose phosphate broth may be obtained in a known manner. Fetuin may be derived from fetal calf serum, for example, while cytochrome c may be derived from horse heart, for example. These protein extracts may all be commercially available ones. For example, lactalbumin hydrolysate may be from Difco (No. 5996), and yeastolate may be prepared for cell culture (TC(tissue culture) yeastolate), such as from Difco (No. 5577), and tryptose phosphate broth may be from Difco (No.0060). Further, fetuin may be from Sigma (No. F2379), cytochrome c may be from Sigma (No. C2506), and inosine may be from Wako Pure Chemical Industries, Ltd.

The individual content of lactalbumin hydrolysate, yeastolate, and tryptose phosphate broth in the medium should preferably be in the range of from 500 to 3000 mg per 1 L of the medium, more preferably in the range of from 1000 to 3000 mg, and most preferably in the range of from 1000 to 2000 mg. The content of fetuin should preferably be in the range of from 1 to 100 mg per 1 L of the medium, more preferably in the range of from 1 to 50 mg, and most preferably in the range of from 5 to 15 mg. The content of cytochrome c should preferably be in the range of from 1 to 500 mg per 1 L of the medium, more preferably in the range of from 1 to 100 mg, and most preferably in the range of from 10 to 100 mg. The content of inosine should preferably be in the range of from 1 to 500 mg, more preferably be in the range of from 1 to 200 mg, and most preferably be in the range of from 10 to 200 mg. The content of bovine plasma albumin V should preferably be in the range of from 1000 to 10000 mg, more preferably be in the range of from 100 to 10000 mg, and most preferably be in the range of from 1000 to 10000 mg.

As the viscosity-supplementing agent contained in the primary cell culture medium according to the present invention, polyvinylpyrrolidone is used. Examples of polyvinylpyrrolidone include, e.g., polyvinylpyrrolidone K-25, polyvinylpyrrolidone K-30, and polyvinylpyrrolidone K-90. Though any of these may be used, polyvinylpyrrolidone K-90, such as, e.g., one manufactured by Wako Pure Chemical Industries, Ltd. (their catalog No. 168-03115), is preferably used. The content of polyvinylpyrrolidone should preferably be in the range of from 100 to 1000 mg per 1 L of the medium, more preferably be in the range of from 100 to 500 mg, and most preferably be in the range of from 200 to 500 mg.

The mixed composition of inorganic salts, sugar composition, mixed composition of amino acids, and mixed composition of vitamins that are added may be ones that can generally be added in an animal cell medium. The mixed composition of inorganic salts may contain $NaH_2PO_4$, $NaHCO_3$, $KCl$, $CaCl_2$, $CuCl_2$, $CoCl_2$, $FeSO_4$, $MgCl_2$, $MgSO_4$, $MnCl_2$, $NaCl$, $NaH_2PO_4$, $(NH_4)_6(Mo_7O_{24}.4H_2O)$, and $ZnCl_2$. The sugar composition may contain glucose, fructose, sucrose, malic acid, α-ketoglutaric acid, succinic acid, fumaric acid, and maltose. The mixed composition of amino acids may contain α-alanine, β-alanine, arginine, asparagine, aspartic acid, cysteine, glutamic acid, glutamine, glycine, histidine, isoleucine, leucine, hydroxyproline, lysine, methionine, phenylalanine, proline, serine, threonine, tryptophan, tyrosine, and valine. The mixed composition of vitamins may contain biotin, D-calcium pantothenate, choline chloride, folic acid, i-inositol, nicotinic acid, pyridoxine, riboflavin, thiamin, vitamin $B_{12}$, para-aminobenzoic acid. Preferably, the mixed composition of inorganic salts, sugar composition, mixed composition of amino acids, and mixed composition of vitamins should contain all of the above substances. They may, however, lack some of the above substances, or be added with other substances. They may all be commercially available ones. There may also be used a commercially available inorganic salt composition, sugar composition, mixed composition of amino acids, and vitamin composition for addition into media. Alternatively, the above-mentioned protein extracts and viscosity-supplementing agent may be added to a known medium containing inorganic salts, sugars, amino acids and vitamins as principal constituents. In this case, examples of the known medium include known insect cell culture media such as Grace's medium and Schneider's Drosophila medium. Further, antibiotics such as penicillin and streptomycin, and glutathione may be added to the medium. In other words, the medium according to the present invention includes all the media that contain at least lactalbumin hydrolysate, yeastolate, tryptose phosphate broth and polyvinylpyrrolidone.

When the medium according to the present invention is used for culturing, it is preferable to add animal serum such as, e.g., fetal bovine serum, or insect lymph, for example. The amount of the serum or lymph added is in the range of from a few % to 30%.

The insect cell primary culture medium according to the present invention can be obtained by mixing medium additives comprising lactalbumin hydrolysate, yeastolate, tryptose phosphate broth and polyvinylpyrrolidone, with other protein extract mixed compositions, mixed compositions of inorganic salts, sugar compositions, mixed compositions of amino acids, and mixed compositions of vitamins. Accordingly, a medium additive comprising at least lactalbumin hydrolysate, yeastolate, tryptose phosphate broth and polyvinylpyrrolidone is included in the scope of the present invention.

One example of the primary cell culture medium according to the present invention is MX medium.

The primary cell culture medium according to the present invention can be prepared by dissolving in pure water the above-mentioned protein extracts, viscosity-supplementing agent, inorganic salt mixed compounds, sugar compounds, amino acid mixed compounds, and vitamin mixed compounds. There is further added a required amount of the above-mentioned animal serum or insect lymph. If necessary, pH is adjusted with an acidic solution such as, e.g., hydrochloric acid, or a basic solution such as, e.g., sodium hydroxide. The pH should preferably be in the range of from 6.0 to 7.0, most preferably in the range of from 6.2 to 6.5.

2. Use of the Medium According to the Invention for Primary Cell Culture

The medium according to the present invention can be used for primary culture of any and all insect cells. It is particularly suitable for insects of the orders Lepidoptera, Diptera, Coleoptera, and Hemiptera, for example. Further, a culture cell line can be created in a short period of time from any and every tissue of these insects. Particularly, the inventive medium is suitable for culturing from embryonic tissue, fat body tissue, reproductive tissue of testis or ovary, digestive system tissue, nervous system tissue, and muscular system tissue. Thus, with the medium according to the present invention, it is possible to create a culture cell line in a short period of time even from the tissue of testis, for example, from which creation of a culture cell line has formerly been believed difficult.

A tissue from which a culture cell line is desired to be created is extracted from an insect in an aseptic manner, and then put into a cell culture vessel such as a cell culture flask, together with the medium according to the present invention. The tissue is cultured for two to three months while exchanging or supplementing the medium as needed. In this way, multiplied cell populations can be transplanted into a new flask in a shorter period of time than possible in the prior art. In this case, culture conditions may be those for conventional insect cell culture. For example, the cells may be cultured in an incubator at temperatures in the range of from 20 to 28° C. The created culture cell line can be cultured after being transferred to a known subculture medium such as, e.g., MGM-464 medium, IPL-41 medium, Grace's medium, EXCELL 400-line medium, Sf900II medium, Schneider medium, etc. Thus, compared with conventional media, a faster transfer to subculture can be achieved with the medium according to the present invention. Alternatively, the cells may be cultured continuously on the medium according to the present invention. Even if the proportion of the serum content added to the medium of the present invention is decreased, the cells can nevertheless divide and multiply well, so the cells can be subcultured over a long period of time.

3. Extracellular Matrix According to the Invention

In the present specification, the term "extracellular matrix" refers to a matrix, substrate or carrier to which cells can adhere and divide and multiply during cell culture. Preferably, the extracellular matrix is used for coating the cell culture surface of the culture vessel.

The extracellular matrix according to the present invention comprises as a principal constituent, an insect-derived, water-soluble chitin that has been subjected to deacetylation as the sole chemical modification.

The water-soluble chitin may be derived from any insect. Preferably, it is extracted from exuviae of the pupa of an insect, particularly silkworm.

The water-soluble chitin according to the present invention can be obtained by the following manner.

A 1 N solution of hydrochloric acid is poured on silkworm pupa exuviae. The exuvia is treated in an environment filled with nitrogen gas at 100° C. for 20 min. Then, protein is removed in a 1 N solution of sodium hydroxide at 80° C. over a period of 36 hours, thereby preparing chitin. To prepare a water-soluble chitin, the chitin is dissolved in a concentrated alkali water solution at room temperature, and the high-viscosity alkaline chitin water solution is allowed to stand at room temperature for a long time to thereby deacetylate in a random manner. Water solubility is exhibited only when the degree of deacetylation is in the range of from 45 to 55%.

For the preparation of the water-soluble chitin for the extracellular matrix according to the present invention, preferably a chitin with high affinity for water should be selected. The affinity of chitin for water can be evaluated according to the method of Brunauer, et al. (J. Amer. Chem. Soc. 62, 1723–1732 (1940)). Namely, the evaluation can be performed by measuring the amount of moisture absorption at each relative humidity by an indirect method using a saturated solution of salts, and by using the BET equation. In the preparation of the chitin suitable for the extracellular matrix according to the present invention, the internal surface area of the material chitin should preferably be 180 $m^2/g$ or more.

Thus, by evaluating the affinity for water of the chitin extracted from an insect, it is possible to use only chitin that has been evaluated to have a high affinity for water as the extracellular matrix for the present invention. In this sense, the water-soluble chitin prepared from the pupa of an insect, particularly from silkworm pupa exuviae is superior. The chitin prepared from silkworm pupa exuviae has a large internal surface area, with more water molecule adsorption sites than other silkworm-derived cuticle. The chitin also has a high heat of adsorption, and its affinity for water is greater than Tensan (Japanese silkworm moth), Sakusan (Chinese silkworm moth), and cicadae. Further, the chitin derived from silkworm pupa exuviae has the same level of affinity for water as that of chitin derived from crabs and lobsters. One example of the silkworm that can be used in the present invention is a polyphagous silkworm race (adapted to new low cost artificial diet (LPY) lacking mulberry leaf powder) (N601×N602)×(C602×C603) (nicknamed "shin-asagiri").

The thus obtained chitin is deacetylated in the following manner to thereby obtain the insect-derived water-soluble chitin according to the present invention.

Deacetylation means the removal of an acetyl group from chitin. Deacetylation can be performed by treating the above-extracted water-soluble chitin with alkali or acid, preferably concentrated alkali or acid. This treatment may involve heating. The treatment may also be performed by a reaction such as Clemmenssen reduction. However, by treating with a concentrated alkaline solution to take advantage of the fact that chitin dissolves in concentrated alkaline, the deacetylation can be performed in a homogeneous system.

The chitin according to the present invention is used after deacetylation, i.e., after removal of the N-acetyl group. While conventional chitin derived from crustaceans has been subjected to a variety of chemical modifications such as, e.g., acylation, tosylation, and carboxylmethylation, the water-soluble chitin according to the invention may only need be subjected to deacetylation. Preferably, deacetylation is performed in a homogeneous system to take advantage of the chitin's solubility in a concentrated alkaline solution. Since in a reaction in a heterogeneous system, N-acetyl groups are preferentially removed from the chitin molecule surface and amorphous portion, there arises a deviation in the distribution of N-acetyl groups. On the other hand, deacetylation proceeds in a random manner in a homogeneous system, so that remaining N-acetyl groups are distributed in a dispersed manner. As a result, hydrogen bonding between chitin molecules weakens, and water-solubility develops. Specifically, it is reported that partially deacetylated chitin with a deacetylation degree in the range of from 40 to 60% dissolves in water (Kramer. K. J et al., Insect Biochem., 14(3), pp. 293–298 (1984)).

Thus, deacetylation is performed in a homogeneous system with the use of a chitin-added, high-viscosity alkaline solution, with the reaction conditions being set such that the degree of deacetylation is in the range of from 45 to 55%. Partially deacetylated chitin may be identified based on an FT-IR. (Fourier transform infrared spectroscopy) spectrum. The degree of deacetylation may be easily measured by IR (infrared) spectroscopy. As chitin is turned into partially deacetylated chitin by deacetylation, absorption by amide groups specific to the N-acetyl group decreases. Accordingly, the degree of deacetylation can be inferred based on the IR spectrum. Specifically, the deacetylation degree may be measured based on the ratio of $A_{1560}/A_{1070}$, where the amide II band of 1560 $cm^{-1}$ in the IR spectrum is used as a characteristic band for quantitation, and a band of 1070 or 1039 $cm^{-1}$ is used as an internal standard. The degree of deacetylation may also be determined by using an analytical curve which has been prepared in advance with reference to a deacetylated chitin sample as a control.

Thus, the insect-derived water-soluble chitin that has been deacetylated as the sole chemical modification according to the present invention has high affinity for water, with a deacetylation degree in the range of from 40 to 60%, preferably from 45 to 50%.

The thus obtained insect-derived water-soluble chitin that has been deacetylated as the sole chemical modification comprises 40–60% chitin, and the remaining 40–60% has a chitosan structure. In other words, the insect-derived water-soluble chitin that has been subjected to deacetylation as the sole chemical modification has high affinity for water, of which 40–60% is chitin and the remaining 40–60% is chitosan. Since the cell membrane surface is negatively charged, the cells attach to the positively charged amino groups of the chitosan and can divide and multiply. This water-soluble chitin can be used as the extracellular matrix.

The water-soluble, partially deacetylated chitin has about six times more water adsorption than prior to treatment and exhibits a high hygroscopicity, making it also suitable for use in food and cosmetics fields as a moisture retention or absorption agent.

4. Use of the Extracellular Matrix According to the Invention

The water-soluble chitin according to the present invention is dissolved in water at a concentration of 0.001 to 1% (W/V). The solution is then poured in the cell culture vessel in such a manner as to spread over the cell attached surface, and air-dried, thereby attaching the water-soluble chitin to the surface of the culture vessel and thus coating the same.

A good coating can be obtained by, for example, putting 0.5 mL of the aqueous solution of chitin per 200 $mm^2$ of the cell culture flask surface into the vessel and air-drying.

Accordingly, the scope of the present invention includes the culture vessels including, e.g., a culture flask, petri dish, and plate whose inner surface is partially or entirely coated by the extracellular matrix according to the invention.

By culturing an insect cell in the cell culture vessel coated with the extracellular matrix according to the invention, the cell can attach to the culture vessel and successfully multiply and divide.

5. Preparation of an Insect Culture Cell Line Using the Insect Cell Primary Culture Medium and the Deacetylated, Insect-derived Chitin According to the Invention By using a vessel coated with the deacetylated, insect-derived chitin according to the invention, an insect culture cell line can be efficiently prepared on an insect cell primary culture medium according to the invention.

A tissue is extracted from an insect in an aseptic manner, and the tissue is put into a vessel coated with a deacetylated, insect-derived chitin according to the invention as the extracellular matrix. The insect cell primary culture medium according to the invention to which a fetal bovine serum has been added is also put into the vessel, and culturing is initiated. At this time, the vessel coated with the extracellular matrix should preferably be washed once with a sterile physiological salt solution. An insect of any order may be used, but an insect of the orders Lepidoptera, Diptera, Coleoptera, or Hemiptera, for example, is particularly suitable. Tissue may be of any kind, but particularly suitable are an embryonic tissue, fat body tissue, reproductive tissue such as that of testicles or ovary, digestive tissue, nervous tissue, and muscle tissue. Culturing is continued until the cells emerging from the tissue section onto the culture vessel surface divide repeatedly and reach sufficient numbers. Culture conditions may be those ordinarily used for insect cell culture. During this period, half of the medium in the culture vessel is exchanged with fresh medium at appropriate intervals, such as every one or two weeks, so that cell transmigration from the tissue can be activated. After cell transmigration begins and a number of cell colonies are formed on the culture vessel bottom and have grown large, the content of fetal bovine serum in the fetal bovine serum-added primary culture medium is gradually decreased. For example, 30% fetal bovine serum may be added at the start of culture, and 20% fetal bovine serum may be added when the cell populations have grown large. Thereafter, half of the medium is replaced with a known subculture medium such as MGM-464 medium, IPL-41 medium, Grace's medium, EXCELL 400-line medium, Sf900II medium, and Schneider medium, etc., and subculture is carried out. By replacing half of the medium at appropriate intervals, the cells can be eventually cultured on the target subculture medium.

In the following, the details of the process for the production of a cell line derived from an intestinal tissue of silkworm will be described by way of example.

1. Wash the body surface of an aseptically grown silkworm three times with a sterile Carlson's solution (penicillin 100000 U/100 mL, 0.05% gentamicin, and 0.05% antiformin have been added).

2. Immerse the silkworm in the last Carlson's solution for 1–2 min to terminate the movement of the silkworm.

3. Cut off the tail portion of the silkworm. Strip the thoracic skin by a pair of tweezers. Grasp the head part with the tweezers, and pull out the intestinal tissue. Immerse the intestinal tissue in a Carlson's solution in a petri dish.

4. Collect the Peritrophic membrane with the tweezers.
5. Put it in an Eppendorf tube.
6. Put collagenase I liquid in the Eppendorf tube (4000 U/0.5 g tissue weight/collagenase mL)
7. Allow to stand at 27° C. for 2 hours.
8. Flush-centrifuge in a small desktop centrifuge (Chibitan™) for ten sec.
9. Dispose of the supernatant liquid and wash twice with a balanced salt solution.
10. Pipette strongly.
11. Transfer to a 15 mL disposable centrifugal tube, and centrifuge at 500–800 rpm for 1 min.
12. Dispose of the supernatant liquid. Add a balanced salt solution again, centrifuge at 1000 rpm for 1 min, and dispose of the supernatant liquid. There is obtained a cell aggregate in the form of a pellet.
13. Put in a MX30 medium, transfer to a 24-multiwell plate and culture. Coat the culture surface of the plate in advance with a 0.01% (W/V)-concentration chitin (particularly in the cases of primary culture of a blood corpuscle cell system, ovary, testis or embryo tissue).
14. Culture at 25° C.
15. Replace half of the medium (0.5–0.7 mL) every two weeks.

EXAMPLES

The present invention will hereafter be described in detail by way of Examples. These Examples, however, should not be taken as limiting the technical scope of the present invention.

Example 1

Preparation of a Insect Cell Primary Culture Medium

The following substances were dissolved in purified water in amounts indicated below per 1 L of the medium to prepare a medium, which was used as the MX medium.

(mg/1000 mL medium)

| Composition of mineral salt mixtures | |
|---|---|
| $NaH_2PO_4 \cdot 2H_2O$ | 507 |
| $NaHCO_3$ | 300 |
| KCl | 1720 |
| $CaCl_2 \cdot 2H_2O$ | 750 |
| $CuCl_2 \cdot 2H_2O$ | 0.1 |
| $CoCl_2 \cdot 6H_2O$ | 0.03 |
| $FeSO_4 \cdot 7H_2O$ | 0.28 |
| $MgCl_2 \cdot 4H_2O$ | 1140 |
| $MgSO_4 \cdot 7H_2O$ | 3269 |
| $MnCl_2 \cdot 4H_2O$ | 0.01 |
| NaCl | 1425 |
| $NaH_2PO_4 \cdot H_2O$ | 580 |
| $(NH_4)_6(Mo_7O_{24} \cdot 4H_2O)$ | 0.02 |
| $ZnCl_2$ | 0.02 |
| Composition of sugars | |
| D-glucose | 2917 |
| Fructose | 20.9 |
| Sucrose | 11865 |
| Malic acid | 306 |
| α-ketoglutaric acid | 169 |
| Succinic acid | 27.4 |
| Fumaric acid | 25.2 |
| Maltose | 500 |
| Composition of amino acid mixtures | |
| L-α-alanine | 131.5 |
| β-alanine | 234 |
| L-arginine.HCl | 692 |
| L-asparagine | 797 |
| L-asparaginic acid | 797 |
| L-cystine | 10.5 |
| L-glutamic acid | 1000 |
| L-glutamine | 750 |
| Glycine | 371 |
| L-histidine | 1142 |
| L-isoleucine | 396 |
| L-leucine | 157 |
| L-cystine.2Na | 60 |
| L-hydroxyproline | 400 |
| L-lysine.HCl | 610 |
| L-methionine | 521 |
| L-phenylalanine | 562 |
| L-proline | 396 |
| DL-serine | 559 |
| L-threonine | 173 |
| L-tryptophan | 91.5 |
| L-tyrosine | 21 |
| L-tyrosine.2Na | 180 |
| L-valine | 292 |
| L-histidine | 1142 |
| Composition of vitamin mixtures | |
| Biotin | 0.123 |
| D-calcium pantothenate | 0.089 |
| Choline chloride | 10.85 |
| Folic acid | 0.125 |
| I-inositol | 0.285 |
| Nicotinic acid | 0.165 |
| Pyridoxine.HCl | 0.285 |
| Riboflavin | 0.125 |
| Thiamine.HCl | 0.125 |
| Vitamin $B_{12}$ | 0.12 |
| Para-aminobenzoic acid | 0.245 |
| Composition of protein extracts | |
| Lactalbumin hydrolysate | 1500 |
| TC-yeastolate | 1500 |
| Tryptose phosphate broth | 1500 |
| Fetuin | 10 |
| Cytochrome c | 50 |
| Inosine | 100 |
| Bovine serum albumin V | 5000 |
| Viscosity-supplementing agent | |
| Polyvinylpyrrolidone K-90 | 250 |

To this prepared medium was further added fetal bovine serum (FBS) to 20% (thereby making MX20 medium) and to 30% (thereby making MX30 medium).

The thus prepared media were adjusted to pH 6.3 by potassium hydroxide. The prepared media were sterilized and stored in a Stericup™ (Millipore, SCGV05012) filtering and sterilizing vessel.

Example 2

Preparation of a Deacetylated Insect-derived Water-Soluble Chitin

1. Preparation of Water-Soluble Chitin from Silkworm Pupa Exuviae (i) Preparation Process Five grams of the pupa exuviae of a polyphagous silkworm race (adapted to new low cost artificial diet (LPY) lacking mulberry leaf powder) (N601×N602)×(C602×C603) (nicknamed "shin-asagiri") was put in 300 mL of 1 N aqueous solution of hydrochloric acid, and treated at 100° C. for 20 min in an environment filled with nitrogen gas. Thereafter, the pupa exuvia was washed with warm water and distilled water until it was neutral, and then vacuum-dried. The dried pupa exuvia was then immersed in 300 mL of 1 N solution of sodium hydroxide, and stirred at 80° C. for 36 hours, to thereby remove the protein in the pupa exuvia. As a result, 0.9 g of chitin was obtained.

(ii) Evaluation of Affinity for Water

Hygroscopicity of the obtained chitin was analyzed according to the method of Yano, Bull, Mellon, Ashpole et al. by measuring the moisture uptake at each relative humidity by an indirect method involving a saturated solution of salts, while applying the BET equation.

As a result, since the obtained chitin had a large internal surface area and a high heat of adsorption, the affinity of the chitin for water was evaluated to be high.

(iii) Deacetylation of Chitin

Three grams of the above chitin obtained from silkworm pupa exuvia was added to a 40% solution of sodium hydroxide. The solution was allowed to stand at 25° C. for 70 hours, to thereby deacetylate the chitin in a homogeneous solution system. There was synthesized partially deacetylated chitin in a 74% yield. When the obtained deacetylated chitin was analyzed by IR spectroscopy, the degree of deacetylation was 45–48%. This partially deacetylated chitin exhibited water solubility at room temperature. It was also shown that the water adsorption of the partially deacetylated chitin at the saturated vapor pressure was 6.3 times as much as prior to the treatment, thus indicating a high hygroscopicity.

This deacetylated chitin was used as the extracellular matrix.

Example 3

Production of a Cell Culture Line

Zero-point-five milliliter of a 0.01–0.1% aqueous solution of the above deacetylated, water-soluble chitin derived from silkworm pupa exuvia was poured into individual culturing wells of a culturing multiwell plate (Sumitomo Bakelite, MS-8024R) such that the solution reached the entire bottom surface of the plate. The solution was then air-dried at room temperature to thereby evaporate the liquid component. Thereafter, the culture surface was washed once with a sterile physiological salt solution.

The fat body was extracted from the silkworm larva in an aseptic manner, and several tens of mg of the fat body was put in the wells of the multiwell plate, in which 1.5 mL (per 200 square mm of the bottom area of the wells) of the MX30 medium treated and prepared according to the method of Example 1 had been put. Half of the medium was replaced every 14 days. After 30 days, transmigration of cells from the tissue became active, and, after two to three months, a number of cell populations formed on the culture surface and grew larger. Microscopic observation revealed the cells to be firmly attached to the flask bottom surface. Thereafter, half of the medium was replaced with MX20 medium. Further, half of MX20 medium was replaced every 14 days.

After several replacements and confirming a sufficient growth of the cells, the medium was strongly blown onto the cell populations with the use of a culturing Pasteur pipette, so that the cells could be floated from the culture surface and transplanted into a new culture flask (Falcon, traditional-type flask No. 3018). The procedure of culturing and transplanting into a new flask after cell multiplication was repeated. During this period, the medium was gradually replaced with a 10% FBS-added medium for subculture and, thereafter, the cells were subcultured as an established culture cell line repeatedly to maintain the cells.

Thus, the medium according to the present invention for the primary culture of insect cells is a novel insect cell primary culture medium at least comprising, as protein extracts, lactalbumin hydrolysate, yeastolate, and tryptose phosphate broth, and, as a viscosity-supplementing agent, polyvinylpyrrolidone. By using the medium, a culture cell line can be established from various tissues of insect efficiently in a short period of time.

The insect-derived water-soluble chitin which is deacetylated as the sole chemical modification according to the present invention can be used for coating a cell culture vessel. The coating enables cells to adhere to the culture vessel surface and efficiently grow and divide.

By performing primary culture with the insect cell primary culture medium and the insect-derived water-soluble chitin which is deacetylated as the sole chemical modification according to the present invention, a cell line can be established in a shorter period of time and more efficiently.

What is claimed is:

1. An insect cell culture vessel coated with a silkworm-derived water-soluble chitin having a degree of deacetylation of 45 to 55%, which is prepared by dissolving a silkworm-derived chitin in a concentrated alkali water solution and allowing the resultant high viscosity alkaline chitin water solution to stand.

2. A matrix for cell culture, comprising a silkworm-derived water-soluble chitin having a degree of deacetylation of 45 to 55%, which is prepared by dissolving a silkworm-derived chitin in a concentrated alkali water solution and allowing the resultant high viscosity alkaline chitin water solution to stand.

3. The matrix for cell culture of claim 2 comprising 0.001% to 1% of said silkworm-derived water-soluble chitin.

4. A process of preparing an insect culture cell line comprising culturing cells derived from an insect in a cell culture vessel coated with the matrix for cell culture of claims 2 or 3 using an insect primary culture medium comprising lactalbumin hydrolysate, yeastolate and tryptose phosphate broth as protein extracts and polyvinylpyrrolidone as a viscosity-supplementing agent.

5. The matrix for cell culture of claims 2 or 3, wherein said matrix is in the form of a coating.

6. The matrix for cell culture of claims 2 or 3 wherein said matrix is in the form of a coating obtained by air drying an aqueous solution of said silkworm water-soluble chitin.

* * * * *